US00PP18167P2

(12) United States Plant Patent
Post

(10) Patent No.: US PP18,167 P2
(45) Date of Patent: Oct. 30, 2007

(54) ***CHRYSANTHEMUM* PLANT NAMED 'DELICHITA'**

(50) Latin Name: *Chrysanthemum×morifolium*
Varietal Denomination: Delichita

(75) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 11/212,380

(22) Filed: Aug. 26, 2005

(51) Int. Cl.
*A01H 5/00* (2006.01)

(52) U.S. Cl. ..... Plt./288

(58) Field of Classification Search ..... Plt./288
See application file for complete search history.

(56) References Cited

PUBLICATIONS

"Cheetah" *Chrysanthemum,* PBR CHO0017, UPOVROM.*
"Cheetah" *Chrysanthemum,* PBR 01503198, UPOVROM.*
"Cheetah" *Chrysanthemum,* PBR CHR1803, UPOVROM.*

* cited by examiner

*Primary Examiner*—Georgia Helmer
(74) *Attorney, Agent, or Firm*—C. A Whealy

(57) ABSTRACT

A new and distinct cultivar of *Chrysanthemum* plant named 'Chita', characterized by its incurved decorative-type inflorescences with white-colored ray florets; vigorous growth habit; early flowering response; and good postproduction longevity.

1 Drawing Sheet

Botanical designation: *Chrysanthemum×morifolium.*
Cultivar denomination: 'Delichita'.

BACKGROUND OF THE INVENTION

The present invention relates to a new and distinct cultivar of *Chrysanthemum* plant, botanically known as *Chrysanthemum×morifolium* and referred to by the name 'Delichita'.

The new *Chrysanthemum* is the product of a planned breeding program conducted by the Inventor in 's Gravenzande, The Netherlands. The objective of the breeding program is to create new vigorous cut *Chrysanthemum* cultivars with interesting inflorescence forms and attractive floret coloration.

The new *Chrysanthemum* originated from a cross-pollination on Mar. 26, 2001 in 's Gravenzande, The Netherlands, of the *Chrysanthemum×morifolium* cultivar Zembla, disclosed in U.S. Plant Pat. No. 14,052, as the female, or seed, parent with a proprietary seedling selection of *Chrysanthemum×morifolium* identified as code number 8774, not patented, as the male, or pollen, parent. The new *Chrysanthemum* was discovered and selected by the Inventor as a single plant within the progeny of the stated cross-pollination in a controlled environment in 's Gravenzande, The Netherlands.

Asexual reproduction of the new *Chrysanthemum* by terminal cuttings in a controlled environment in 's Gravenzande, The Netherlands since May 15, 2002, has shown that the unique features of this new *Chrysanthemum* are stable and reproduced true to type in successive generations.

BRIEF SUMMARY OF THE INVENTION

The cultivar Delichita has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Delichita'. These characteristics in combination distinguish 'Delichita'as a new and distinct cultivar:

1. Large incurved decorative-type inflorescences with white-colored ray florets; typically grown as a disbud-type.
2. Vigorous growth habit.
3. Early flowering response.
4. Good postproduction longevity.
5. Relatively tolerant to low temperature conditions.

Plants of the new *Chrysanthemum* can be compared to plants of the female parent, the cultivar Zembla. In side-by-side comparisons conducted in 's Gravenzande, The Netherlands, plants of the new *Chrysanthemum* differed from plants of the cultivar Zembla in the following characteristics:

1. Plants of the new *Chrysanthemum* had larger inflorescences than plants of the cultivar Zembla.
2. Ray florets of plants of the new *Chrysanthemum* were more incurved than ray florets of plants of the cultivar Zembla.
3. Plants of the new *Chrysanthemum* were best grown as disbud-types whereas plants of the cultivar Zembla were best grown as spray-types.

Plants of the new *Chrysanthemum* can be compared to plants of the male parent selection. In side-by-side comparisons conducted in 's Gravenzande, The Netherlands, plants of the new *Chrysanthemum* differed from plants of the male parent selection in the following characteristics:

1. Plants of the new *Chrysanthemum* were more vigorous than plants of the male parent selection.
2. Plants of the new *Chrysanthemum* had larger leaves than plants of the male parent selection.

3. Plants of the new *Chrysanthemum* flowered earlier than plants of the male parent selection.

Plants of the new *Chrysanthemum* can also be compared to plants of the *Chrysanthemum* cultivar Tatyana, disclosed in U.S. Plant patent application Ser. No. 11/119,064. In side-by-side comparisons conducted in 's Gravenzande, The Netherlands, plants of the new *Chrysanthemum* differed primarily from plants of the cultivar Tatyana in the following characteristics:

1. Plants of the new *Chrysanthemum* were more vigorous than plants of the cultivar Tatyana.
2. Plants of the new *Chrysanthemum* had broader leaves with longer leaf petioles than plants of the cultivar Tatyana.
3. Plants of the new *Chrysanthemum* had larger inflorescences than plants of the cultivar Tatyana.
4. Ray florets of plants of the new *Chrysanthemum* were more incurved than ray florets of plants of the cultivar Tatyana.
5. Ray florets of plants of the new *Chrysanthemum* did not "pink" under low temperature conditions whereas ray florets of plants of the cultivar Tatyana "pinked" under low temperature conditions.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Delichita'.

The photograph in the middle of the sheet is a close-up view of a typical inflorescence of 'Delichita'.

The photograph at the bottom of the sheet is a close-up view of the lower and upper surfaces of typical leaves of 'Delichita'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the summer in 's Gravenzande, The Netherlands, under commercial practice in a glass-covered greenhouse. Plants were initially given long day/short night treatments followed by short day/long night treatments to induce flower initiation and development. During the production of the plants, day temperatures averages 20° C. and night temperatures averaged 18° C. Plants were grown as disbud-types and were about ten weeks from planting when the photographs and the description were taken.

Botanical classification: *Chrysanthemum×morifolium* cultivar Delichita.

Commercial classification: Incurved decorative-type *Chrysanthemum* typically grown as a disbud-type cut flower.

Parentage:

*Female, or seed, parent.*—*Chrysanthemum×morifolium* cultivar Zembla, disclosed in U.S. Plant Pat. No. 14,052.

*Male, or pollen, parent.*—Proprietary seedling selection of *Chrysanthemum×morifolium* identified as code number 8774, not patented.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 12 days at 20° C.

*Time to produce a rooted cutting, winter.*—About 14 days at 18° C.

*Root description.*—Fine and freely branching; white in color.

Plant description:

*Appearance.*—Herbaceous incurved decorative-type cut *Chrysanthemum;* typically grown as a disbud-type; erect and strong flowering stems.

*Growth rate.*—Moderate; vigorous.

*Flowering stem description.*—Length: About 80 to 90 cm. Diameter: About 9 mm. Strength: Strong. Aspect: Erect. Color: 146C.

*Foliage description.*—Arrangement: Alternate. Length: About 10.5 to 14 cm. Width: About 8 to 9 cm. Apex: Cuspidate. Base: Attenuate. Margin: Pinnately lobed. Texture, upper and lower surface: Pubescent; rough. Petiole length: About 2 to 3.5 cm. Color: Developing foliage, upper surface: 147A. Developing foliage, lower surface: Between 137B and 147B. Fully expanded foliage, upper surface: 137A. Fully expanded foliage, lower surface: 147B. Venation, upper and lower surface: 146C. Petiole, upper and lower surfaces: 146C.

Inflorescence description:

*Appearance.*—Incurved decorative-type inflorescence form with lanceolate to oblong-shaped ray florets. Large inflorescences borne on terminals above foliage. Disk and ray florets develop acropetally on a capitulum. Inflorescences not fragrant. Typically grown as a disbud-type.

*Flowering response.*—Under natural conditions, plants typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 49 days later. Early and uniform flowering response.

*Postproduction longevity.*—Cut inflorescences will maintain good substance and form for about 3.5 weeks.

*Quantity of inflorescences per flowering stem.*—Grown as a disbud-type, only one inflorescence per flowering stem is allowed to develop. Grown as a spray-type, about eight to eleven inflorescences develop.

*Inflorescence size.*—Diameter: About 14 to 15 cm. Depth (height): About 4 to 4.5 cm. Diameter of disc: About 2 mm.

*Inflorescence buds.*—Length: About 1 to 1.5 cm. Diameter: About 1.2 to 1.5 cm. Shape: Oblate. Color: Close to 137C.

*Ray florets.*—Length: About 6.5 to 7 cm. Width: About 2.2 to 2.5 cm. Shape: Lanceolate to oblong. Apex: Rounded or emarginate. Base: Fused. Margin: Entire. Texture, upper and lower surfaces: Smooth, glabrous; satiny. Number of ray florets per inflorescence: About 230 in numerous whorls. Color: When opening, upper and lower surfaces: 155A. Fully opened, upper and lower surfaces: Lighter then 155D; towards the base, 144C.

*Disc florets*.—Shape: Tubular. Length: About 5 mm. Width: About 1 mm. Number of disc florets per inflorescence: About five. Color: Apex: N144B. Mid-section: 20B. Base: 145D.

*Peduncles* (*when grown as spray-types*).—Length, terminal peduncle: About 3 to 4 cm. Length, fourth peduncle: About 4 to 5 cm. Diameter: About 6 to 7 mm. Strength: Moderately strong. Texture: Pubescent. Color: Close to 147B.

*Reproductive organs*.—Androecium: Present on disc florets only. Anther color: Close to 9A. Pollen color: Close to 9A. Gynoecium: Present on both ray and disc florets. Stigma size: About 0.5 mm by 7 mm. Stigma color: Towards the apex, 151C; towards the base, close to 144C.

*Seed/fruit*.—Seed and fruit production has not been observed.

Disease/pest resistance: Resistance to known *Chrysanthemum* pests and pathogens has not been observed on plants of the new *Chrysanthemum*.

Temperature tolerance: Plants of the new *Chrysanthemum* have been observed to tolerates temperatures from 14° C. to 35° C.

It is claimed:

1. A new and distinct cultivar of *Chrysanthemum* plant named 'Delichita', as illustrated and described.

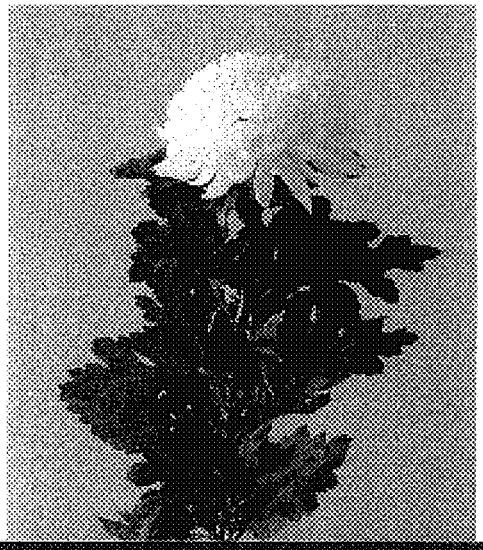
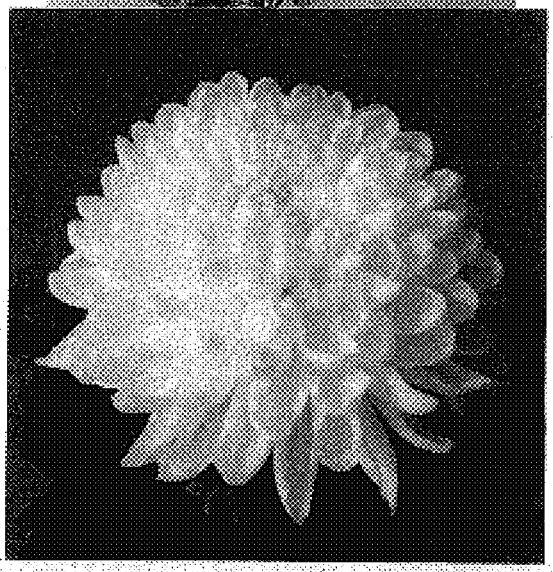
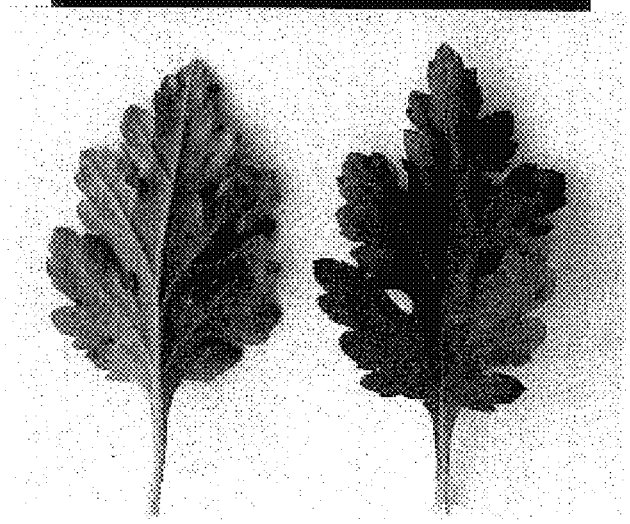

* * * * *